United States Patent [19]

Turk et al.

[11] Patent Number: 4,902,509

[45] Date of Patent: Feb. 20, 1990

[54] PROCESS FOR THE ISOLATION OF CHICKEN EGG CYSTATIN, ANTIVIRAL AGENTS CONTAINING IT AND ITS USE AS VIRAL PROTEASE INHIBITOR

[75] Inventors: Vito Turk; Jože Brzin, both of Ljubljana, Yugoslavia

[73] Assignee: KRKA, tovarna zdravil, n.sol.o., Yugoslavia

[21] Appl. No.: 113,963

[22] Filed: Oct. 29, 1987

Related U.S. Application Data

[62] Division of Ser. No. 818,307, Jan. 13, 1986, abandoned.

[30] Foreign Application Priority Data

Jan. 16, 1985 [YU] Yugoslavia ............................ P58/85

[51] Int. Cl.$^4$ ...................... A61K 35/48; A61K 37/02
[52] U.S. Cl. ......................................... 424/105; 514/2; 514/12; 514/21; 530/362; 530/364
[58] Field of Search .................. 530/362, 364; 514/21, 514/12, 2; 424/105

[56] References Cited

PUBLICATIONS

Schwabe, *The Biochemical Journal*, 217(3), 813–817, (1983).
Anastasai, *The Biolochemical Journal*, 211(1), 128–138, (1983).
Turk, *Chem. Abst.*, 100, 222, (1984), Abst. No. 81820a.
Korant, *Chem. Abst.*, 102, 445, (1985), Abst. No. 164716p.
Korant, *Biochem. Biophys. Res. Commun.*, 127(3), 1072–1076, (1985).

*Primary Examiner*—Margaret Moskowitz
*Assistant Examiner*—F. T. Moezie
*Attorney, Agent, or Firm*—Pollock, VandeSande & Priddy

[57] ABSTRACT

There is suggested a new process for the isolation of chicken egg white cystatin from an aqueous solution of chicken egg white by means of heating to max. 80° C., chromatography on carboxymethylated papain-Sepharose 4B, chromatography on Sephadex-G-50 and purification by means of ion exchange chromatrography of the Fast Protein Liquid Chromatrography type. There are further suggested new agents and methods of treating viral infections in living organisms, especially mammalian and avian picornaviral infections, by means of chicken egg white cystatin.

4 Claims, No Drawings

PROCESS FOR THE ISOLATION OF CHICKEN EGG CYSTATIN, ANTIVIRAL AGENTS CONTAINING IT AND ITS USE AS VIRAL PROTEASE INHIBITOR

This application is a division of Ser. No. 818,307, filed on Jan. 13, 1986 now abandoned.

The invention deals with the isolation of a chicken egg white cystatin, with antiviral agents containing it and its use as a specific inhibitor of proteolytic processing of viral proteins.

It is known that living organisms contain proteolytic enzymes and their corresponding inhibitors, which participate in the processes of regulation and control of various biological functions in normal and pathological conditions of organisms. It is also known that proteolytic enzymes participate in the formation of some biologically active proteins from their precursors. Thus, proteolytic enzymes of many animal viruses, e.g. picornaviruses, play a crucial role in the viral replication. Viral proteases cleave the precursor proteins into smaller products and the cleavage products assemble into larger and more complex viral structures (J. Putnak and B. Phillips, Microb. Rev. 45, 287 (1982)). Therefore, the protease inhibitors represent potential therapeutical substances as well.

It is known that the picornavirus protease is very sensitive to inhibitors of thiol proteases, e.g. mercurials, iodoacetate, $\alpha_2$-macroglobulin and others (B. D. Korant, K. Lonberg-Holm and P. LaColla, in: Targets for the design of antiviral agents, E. De Clercq and R. T. Walker, eds., Plenum Press, pp. 61–98, 1984). A specific inhibitor of thiol proteases is also low $M_r$ protein chicken cystatin, isolated from egg white (A. Anastasi, M. A. Brown, A. A. Kembhavi, M. J. H. Nicklin, C. A. Sayers, D. C. Sunter and A. J. Barrett, Biochem. J. 211, 129–138, 1983; V. Turk et al., Hoppe-Seyler's Z. Physiol. Chem. 364, 1487–1496, 1983). Chicken cystatin was isolated in two forms, which differ in their isoelectric points, with pI 5.6 and 6.5. Its amino acid sequence was also determined (V. Turk et al., Hoppe-Seyler's Z. Physio. Chem. 364, 1487–1496, 1983; C. Schwabe et al., Biochem. J. 214, 813–817, 1984). Chicken egg cystatin was found to be a very potent inhibitor of plant proteinase papain and mammalian proteinases cathepsins B, H and L (A. Anastasi et al., Biochem. J. 211, 129–138, 1983).

Although the published methods for isolation have given pure products, the yield was rather low.

As the first subject of invention we therefore propose a new process of isolating chicken cystatin from egg whites as a natural source. An aqueous solution of chicken egg white was heated to max. 80° C. (optimally 60°–70° C.) to precipitate inactive proteins. The solution was then cooled and centrifuged. To the clear supernatant 1M NaCl was added and affinity chromatography was carried out on carboxymethylated (Cm) papain-Sepharose 4B with 0.01M Tris buffer, pH 8.0, in the presence of 1.0M NaCl. The inhibitor cystatin was eluted with 0.01M NaOH, pH 11.5, concentrated with ultrafiltration or liophylization, and chromatographed on Sephadex G-50 in 0.01M Tris buffer, pH 8.0. The inhibitory active fractions were collected, concentrated by ultrafiltration and chromatographed by the method of Fast Protein Liquid Chromatography (FPLC, Pharmacia, Sweden) on the mono Q column (Pharmacia, Sweden) with the starting buffer 0.01M Tris, pH 8.0, and the inhibitor chicken cystatin was eluted with the addition of 0.5M NaCl to the starting buffer. The inhibitor was eluted in two inhibitory peaks with pI values of 5.6 and 6.5, determined by isoelectric focusing.

All chemicals used in the process are commercially known and available. The process of isolating chicken cystatin by the proposed invention is technologically simple and gives higher yields than the hitherto described methods.

In our experiments we have surprisingly found that the chicken egg white cystatin inhibits the proteolytic activity of picornaviruses. Picornaviruses include e.g. poliovirus, rhinovirus and etiological agents of hepatitis A and foot and mouth disease.

The inhibitory activity of chicken egg which cystatin is evident from the results presented in the Table. Therefore a further object of the invention is the use of chicken egg white cystatin for the treatment of picornavirus infections in mammals and birds, and all other living beings infected by corresponding viruses.

An object of the invention are also antiviral agents containing chicken egg white cystatin in physiologically acceptable amounts, in quantities effective for the inhibitiion of proteolytic activity of picornaviruses. The formulation and application of these antiviral agents is within the limits of knowledge and experience of a person skilled in the art.

It should be noted that, although in the present application there is only discussed chicken egg white cystatin obtained in accordance with the inventive process, we also propose the use of chicken cystatin prepared by the method of genetic engineering.

The inventions are illustrated but not limited by the following Examples.

The isolation of chicken egg white cystatin

EXAMPLE 1

The egg whites from 100 eggs were diluted with an equal volume of distilled water and homogenized with Waring blendor. The solution was heated in a water bath at 60° C. and after 15 min cooled in cold water bath. The precipitate was centrifuged in refrigerated centrifuge Sorvall RC-2B at 15000×g for 30 min and to the supernatant NaCl (crystalline) up to 1M was added. The solution was then divided into 5 aliquots and applied to Cm-papain Sepharose 4B column (prepared according to Anastasi. A. et al., Biochem. J. 211, 129–138, 1983) prepared in a glass beaker, washed with 0.01M Tris buffer, pH 8.0, containing 1M NaCl and then chicken cystatin was eluted with 0.01M NaOH, pH 11.5. The obtained fractions were concentrated by ultrafiltration on Amicon YM-5 membrane to 1/5 of the initial volume and applied to the Sephadex G-50 column (6×110 cm) which was equilibrated with 0.01M Tris buffer, pH 8.0 containing 1M NaCl. The eluted protein fractions containing the inhibitory activity were pooled, concentrated by ultrafiltration on Amicon YM-5 membrane to 50 ml and then chromatographed by 10 ml on FPLC on mono Q column with the starting buffer 0.01M Tris, pH 8.0, and then eluted with the gradient, obtained by the addition of 0.5M NaCl. The inhibitor was eluted into two peaks with pI values of 5.6 and 6.5. The total yield was 32% with respect to the starting content of chicken egg cystatin in egg white.

The inhibitory activity of chicken cystatin was determined with papain as test enzyme using Bz-DL-Arg-2-naphtylamide (Bz-ArgNap) as substrate according to the published method (A. J. Barrett, Anal. Biochem. 37, 280–293, 1972). One unit of the inhibitory activity corresponds to the total inhibition of 1 μg of papain.

EXAMPLE 2

The egg whites from 100 eggs were diluted with an equal volume of distilled water and homogenized using Waring blendor. The solution was heated in a water bath up to 80° C. and after 15 min cooled in a water bath. The further experimental procedure is the same as described in Example 1. The yield was about 27% which was just a little lower than in Example 1.

The test of biological activity

The inhibition of virus production in human HeLa cells teated with chicken egg white cystatin The experiment was carried out with human HeLa cells, strain 0 (B. Korant et al., Virology 48, 71–86, 1972) or human WISH cells (Americal Type Culture Collection CCL 25).

The cells were grown as monolayer cultures in plastic petri dishes in Mc Coy 5A medium and 10% calf serum as previously described (B. Korant et al., Virology 48, 71–86, 1972). The viruses used in the experiments were poliomyelitis virus type 1, strain Mahony, and virus of vesicular stomatitis (member of rhabdo viruses not requring extensive protein cleavage in the process of replication).

Virus growth and plaque titrations were carried out by standard methods (B. Korant et al., Virology 48, 71–86, 1972). Labelling of virus-infected or control cells was carried out by addition of $^{35}$S-L-Metionina (1200 Ci/mmole) to a specific activity of 50 μCi/ml in methionin-free medium. Analysis of labelled proteins was carried out in polyacrylamide slab gels containing sodium dodecyl sulphate (SDS) as described (B. Korant et al., Proc. Natl. Acad. Sci. USA, 76, 2992–2995, 1979). Stained, dried gels were autoradiographed using DuPont Cronex 4X-ray film.

The results are presented in the Table.

TABLE

The inhibiiton of poliovirus production in human HeLa cells treated with chicken egg white cystatin (100 μM).

| Virus | % of inhibition |
|---|---|
| Poliomyelitis virus type 1(Mahony) | 80% +/− 5% |
| Rhinovirus type 1A | 73% +/− 8% |
| Vesicular stomatitis virus | 7% +/− 4% |

From the obtained results in the Table it is evident that chicken egg white cystatin shows antiviral effect reducing virus production of poliovirus and rhinovirus.

What we claim is:

1. A method of treating picornaviral infection in a mammal or bird which comprises administering a therapeutically effective, and physiologically acceptable, amount of chicken egg white cystatin to a mammal or bird suffering from a picornaviral infection.

2. The method of claim 1 wherein said picornaviral infection is poliovirus in humans.

3. The method of claim 1 wherein said picornaviral infection is rhinovirus in humans.

4. The method of claim 1 wherein said chicken egg white cystatin is formulated with conventional additives.

* * * * *